(12) United States Patent
Youn et al.

(10) Patent No.: US 11,298,353 B2
(45) Date of Patent: Apr. 12, 2022

(54) ANTI-INFLAMMATORY COMPOSITION

(71) Applicant: OSTEONEUROGEN INC., Seoul (KR)

(72) Inventors: Byung Soo Youn, Seoul (KR); Han Soo Kim, Seoul (KR); Ik Hwan Kim, Seoul (KR); Ho Sup Yoon, Nanyang (SG); Moon Kee Maeng, Seoul (KR); Baik Lin Seong, Seoul (KR); Min Ju Ham, Seoul (KR); Hyeong Deok Choi, Incheon (KR)

(73) Assignee: OSTEONEUROGEN INC., Seoul (KR)

( * ) Notice: Subject to any disclaimer, the term of this patent is extended or adjusted under 35 U.S.C. 154(b) by 27 days.

(21) Appl. No.: 16/719,913

(22) Filed: Dec. 18, 2019

(65) Prior Publication Data
US 2021/0060007 A1    Mar. 4, 2021

(30) Foreign Application Priority Data

Aug. 30, 2019  (KR) .................. 10-2019-0107687

(51) Int. Cl.
*A61K 31/496* (2006.01)
*A61P 29/00* (2006.01)

(52) U.S. Cl.
CPC ............ *A61K 31/496* (2013.01); *A61P 29/00* (2018.01)

(58) Field of Classification Search
CPC ............................ A61K 31/496; A61P 29/00
See application file for complete search history.

(56) References Cited

U.S. PATENT DOCUMENTS 10,370,364 B1    8/2019  Youn et al.

FOREIGN PATENT DOCUMENTS

| KR | 10-0023546 B1 | 2/1987 |
| KR | 10-2010-0038919 A | 4/2010 |
| KR | 10-1540085 B1 | 7/2015 |
| KR | 10-1604257 B1 | 3/2016 |
| KR | 10-1871166 B1 | 7/2018 |

OTHER PUBLICATIONS

Wynn et. al., Nature Med., publ. 2012, vol. 18(7), pp. 1028-1040 (Year: 2012).*
English translation of KR 10-187116 B1, publ. Jul. 2, 2018, pp. 1-17 (Year: 2018).*
Farrell et. al., Gut & Liver, publ. 2012, vol. 6(2), pp. 149-171 (Year: 2012).*
Caligiuri et. al., Int. J. Mol. Sci., vol. 17, pp. 1-34, publ. 2016 (Year: 2016).*
Sorrentino et. al., Dig. Dis. Sci., vol. 59, pp. 699-701, publ. 2014 (Year: 2014).*

* cited by examiner

*Primary Examiner* — Sarah Pihonak
(74) *Attorney, Agent, or Firm* — Revolution IP, PLLC

(57) ABSTRACT

The present invention relates to an anti-inflammatory composition, and more particularly to an anti-inflammatory composition containing, as an active ingredient, a compound represented by Formula 1 or a salt thereof, wherein the anti-inflammatory composition may inhibit inflammatory response even at an early stage by inhibiting the interaction between CD14 and LPS and blocking the expression of CD14 and the expression of TNFα and IL-1β, which are the key factors in inflammatory response, and may also regulate the expression of important factors, such as CCL2 (MCP-1), CCL7 (MCP-3), CXCL2, CHOP and NOX1, which are involved in inflammatory response.

5 Claims, 14 Drawing Sheets

Formula 1

Control

LPS

LPS + ONG41008

LPS (100ng/ml)

LPS (100ng/ml) + ONG41008 50uM

LPS (100ng/ml) + ONG41008 50uM
GAPDH

ANTI-INFLAMMATORY COMPOSITION

BACKGROUND OF THE INVENTION

Field of the Invention

The present invention relates to an anti-inflammatory composition, and more particularly to an anti-inflammatory composition containing, as an active ingredient, a compound represented by Formula 1 or a salt thereof.

Description of the Prior Art

Inflammations are common homeostatic functions in vivo, which are alarm signals against endogenous and exogenous antigens (bacterial, viral, parasitic infections and various stress signals in cells). These alarm signals are sensed by immune cells, inducing innate immunity and adaptive immunity, ultimately maintaining homeostasis of the cells. Thus, inflammatory responses are necessary to maintain a living body normally.

However, if such inflammatory responses occur excessively, biological tissues or organs at the site of inflammation do not maintain their original functions, and undesirable immune dysregulation occurs, leading to pain and fever, which are defined inflammatory diseases.

Excessive inflammatory responses to antigens may occur due to abnormalities in the affinity between immune cells (e.g., dendritic cells and T cells) and co-stimulatory receptor-ligand interaction. In particular, autoreactive T cells break down immune tolerance and cause a variety of inflammatory autoimmune diseases (rheumatic arthritis, Crohn's disease, lupus, nervous multiple sclerosis, etc.).

Thus, there is a need for potent anti-inflammatory agents to cope with these inflammatory diseases, which still constitutes the largest unmet need in the medical community.

The present inventors previously developed a novel compound exhibiting an excellent therapeutic effect against fibrosis (Korean Patent No. 10-1871166). In connection with this compound, the present inventors have conducted further studies and found that the developed compound can be involved in anti-inflammatory responses. Accordingly, the present inventors have conducted further studies on the possibility of the compound as an anti-inflammatory agent in earnest, and as a result, have found that the compound can actually exhibit a very excellent anti-inflammatory effect, thereby completing the present invention.

PRIOR ART DOCUMENTS

Patent Documents

Korean Patent No. 10-1871166

SUMMARY OF THE INVENTION

It is a main object of the present invention to provide an anti-inflammatory composition exhibiting an excellent inhibitory effect on inflammatory response.

Another object of the present invention is to provide a method of treating an inflammatory disease in a subject in need thereof.

In accordance with one aspect of the present invention, the present invention provides an anti-inflammatory composition containing, as an active ingredient, a compound represented by the Formula 1:

[Formula 1]

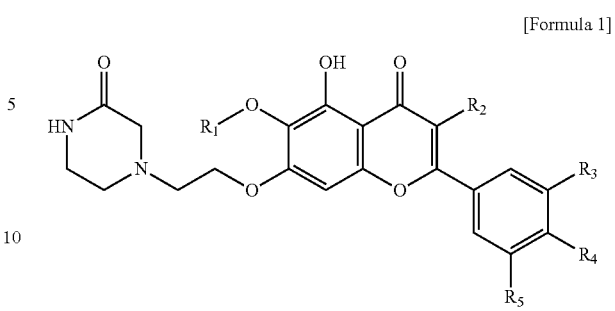

or a salt thereof, wherein $R_1$ is $C_{1-5}$ alkyl, $C_{5-6}$ cycloalkyl, $C_{5-6}$ heterocycloalkyl, $C_{6-12}$ aryl or $C_{5-6}$ heteroaryl, where the $C_{5-6}$ heterocycloalkyl or $C_{5-6}$ heteroaryl each independently contain at least one heteroatom selected from the group consisting of oxygen and nitrogen; $R_2$ is hydrogen, ethyl, acetyl, acetoxy, carboxy, benzoyloxy or 3,4,5-trihydroxybenzoyloxy; $R_3$ is hydrogen, hydroxy, methyl, methoxy, acetoxy, carboxy or benzoyloxy; $R_4$ is hydrogen, hydroxy, methyl, methoxy, acetoxy, carboxy or benzoyloxy; and $R_5$ is hydrogen, hydroxy, methyl, methoxy, acetoxy, carboxy or benzoyloxy.

In the composition of the present invention, $R_1$ is preferably methyl, ethyl, cyclopentyl, cyclohexyl or phenyl.

In the composition of the present invention, preferably, $R_1$ is methyl; $R_2$ is hydrogen; $R_3$ is hydrogen, hydroxy or methoxy; $R_4$ is hydroxy or methoxy; and $R_5$ is hydrogen, hydroxy or methoxy.

In the composition of the present invention, the compound is preferably selected from the group consisting of Formula 2, Formula 3, Formula 4 and Formula 5:

[Formula 2]

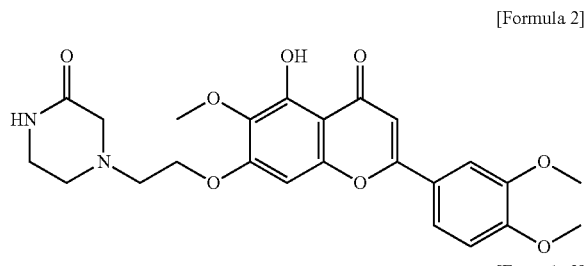

[Formula 3]

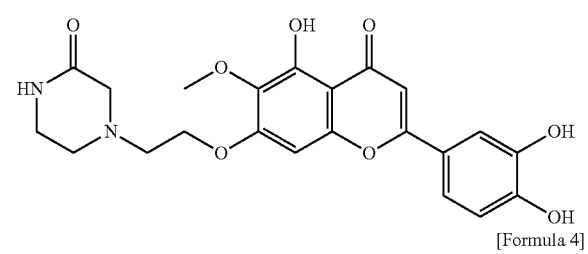

[Formula 4]

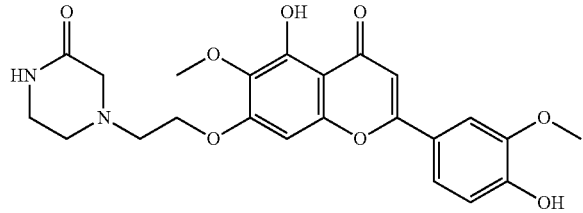

[Formula 5]

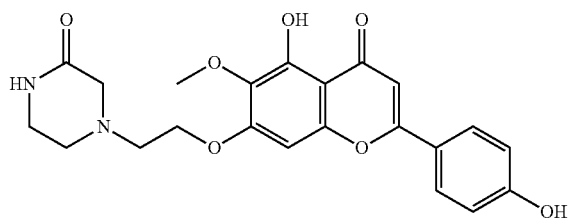

or a salt thereof.

In the composition of the present invention, the composition is preferably a pharmaceutical composition, a quasi-drug composition, a food composition, a food additive composition, a feed composition, a feed additive composition, or a cosmetic composition.

In accordance with another aspect of the present invention, the present invention provides a method of treating an inflammatory disease in a subject in need thereof, comprising: providing a composition comprising, as an active ingredient, a compound represented by the Formula 1:

[Formula 1]

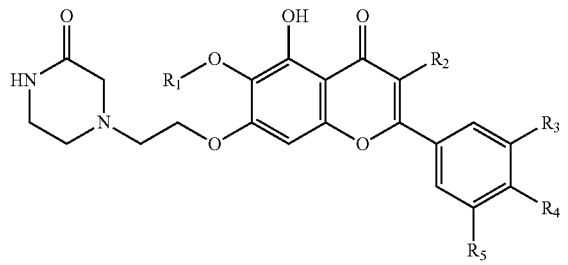

or a salt thereof, wherein $R_1$ is $C_{1-5}$ alkyl, $C_{5-6}$ cycloalkyl, $C_{5-6}$ heterocycloalkyl, $C_{6-12}$ aryl or $C_{5-6}$ heteroaryl, where the $C_{5-6}$ heterocycloalkyl or $C_{5-6}$ heteroaryl each independently contain at least one heteroatom selected from the group consisting of oxygen and nitrogen; $R_2$ is hydrogen, ethyl, acetyl, acetoxy, carboxy, benzoyloxy or 3,4,5-trihydroxybenzoyloxy; $R_3$ is hydrogen, hydroxy, methyl, methoxy, acetoxy, carboxy or benzoyloxy; $R_4$ is hydrogen, hydroxy, methyl, methoxy, acetoxy, carboxy or benzoyloxy; and $R_5$ is hydrogen, hydroxy, methyl, methoxy, acetoxy, carboxy or benzoyloxy; and administering the composition to the subject, wherein the inflammatory disease is treated.

In the method of the present invention, $R_1$ is preferably methyl, ethyl, cyclopentyl, cyclohexyl or phenyl.

In the method of the present invention, preferably, $R_1$ is methyl; $R_2$ is hydrogen; $R_3$ is hydrogen, hydroxy or methoxy; $R_4$ is hydroxy or methoxy; and $R_5$ is hydrogen, hydroxy or methoxy.

In the method of the present invention, the compound is preferably selected from the group consisting of Formula 2, Formula 3, Formula 4 and Formula 5:

[Formula 2]

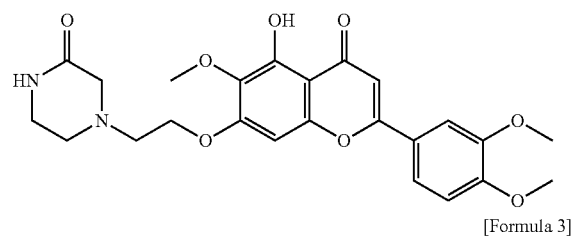

[Formula 3]

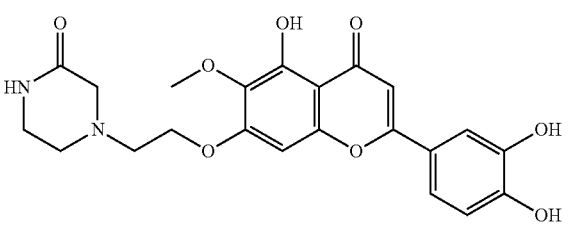

[Formula 4]

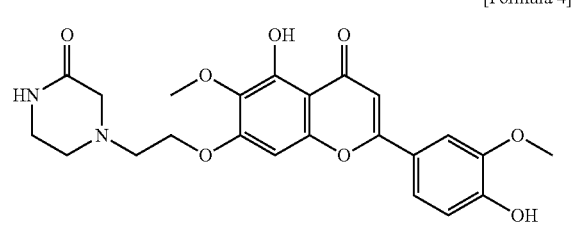

[Formula 5]

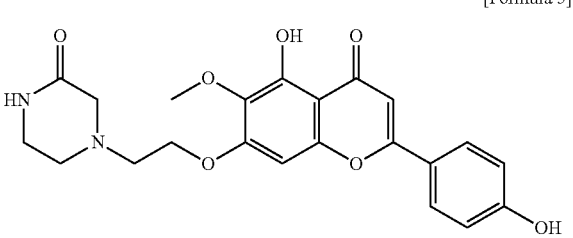

or a salt thereof.

In the method of the present invention, the composition is preferably a pharmaceutical composition, a quasi-drug composition, a food composition, a food additive composition, a feed composition, a feed additive composition, or a cosmetic composition.

In the method of the present invention, the inflammatory disease is preferably selected from the group consisting of inflammatory lung disease, inflammatory liver disease, inflammatory bowel disease, autoinflammatory disease, inflammatory central nervous system disease, inflammatory skin disease, and allergic inflammatory disease.

In the method of the present invention, the inflammatory disease is preferably selected from the group consisting of interstitial lung disease (ILD), non-alcoholic steatohepatitis (NASH), Crohn's disease, ulcerative colitis, rheumatoid arthritis, type 1 diabetes, lupus, multiple sclerosis, Parkinson's disease, scleroderma, and psoriasis.

BRIEF DESCRIPTION OF THE DRAWINGS

FIGS. 10 to 12 are enlarged views of the merge of FIG. 9.

DETAILED DESCRIPTION OF THE INVENTION

Figure 1:
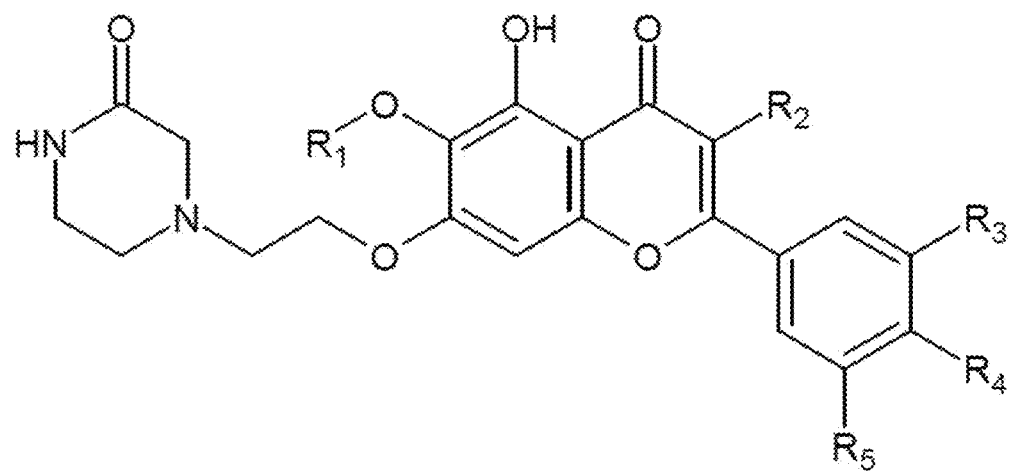
FIG. 1 shows the structure of a compound which is the active ingredient of the composition of the present invention.

The anti-inflammatory composition of the present invention contains, as an active ingredient, a compound represented by the formula 1:

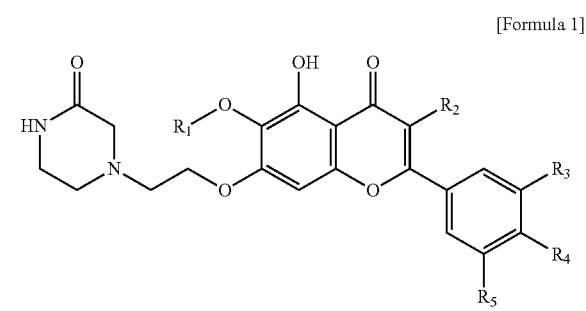

[Formula 1]

or a salt thereof, wherein $R_1$ is $C_{1-5}$ alkyl, $C_{5-6}$ cycloalkyl, $C_{5-6}$ heterocycloalkyl, $C_{6-12}$ aryl or $C_{5-6}$ heteroaryl, where the $C_{5-6}$ heterocycloalkyl or $C_{5-6}$ heteroaryl each independently contain at least one heteroatom selected from the group consisting of oxygen and nitrogen; $R_2$ is hydrogen, ethyl, acetyl, acetoxy, carboxy, benzoyloxy or 3,4,5-trihydroxybenzoyloxy; $R_3$ is hydrogen, hydroxy, methyl, methoxy, acetoxy, carboxy or benzoyloxy; $R_4$ is hydrogen, hydroxy, methyl, methoxy, acetoxy, carboxy or benzoyloxy; and $R_5$ is hydrogen, hydroxy, methyl, methoxy, acetoxy, carboxy or benzoyloxy.

A method for producing the compound is disclosed in Korean Patent No. 10-1871166.

Since the composition of the present invention contains the compound or a salt thereof as an active ingredient, it can inhibit inflammatory response even at an early stage and exhibit a potent anti-inflammatory effect by regulating expression of the key factors of macrophages, which are involved in inflammatory response.

Specifically, the composition of the present invention can inhibit an early stage of inflammatory response by blocking the interaction between CD14 and LPS in the early stage of LPS-induced inflammatory response and blocking the expression of CD14, can strongly inhibit the expression of TNFα and IL-1β, which are the key factors of inflammatory response, and can also strongly inhibit the expression of key factors such as CCL2 (MCP-1), CCL7 (MCP-3), CXCL2, CHOP and NOX1, which are involved in inflammatory response.

As disclosed in Korean Patent No. 10-1871166, it was found that the compound can be absorbed rapidly into the body, can maintain its original structure in vivo for a long time, and is safe for the human body. Therefore, the composition of the present invention can exhibit a rapid and sustained anti-inflammatory effect and will be safe to use in the human body.

In consideration of the anti-inflammatory effect and safety as described above, the active ingredient of the composition of the present invention is a compound or a salt thereof in which $R_1$ in Formula 1 is methyl, ethyl, cyclopentyl, cyclohexyl or phenyl. More preferably, the active ingredient is a compound or a salt thereof in which $R_1$ in Formula 1 is methyl, $R_2$ is hydrogen, $R_3$ is hydrogen, hydroxy or methoxy, $R_4$ is hydroxy or methoxy, and $R_5$ is hydrogen, hydroxy or methoxy. Even more preferably, the active ingredient is a compound represented by any one of Formulas 2 to 5 or a salt thereof.

In this case, the salt of the compound may be in the form of a pharmaceutically acceptable salt, a food-acceptable salt, a feed-acceptable salt or a cosmetically acceptable salt.

Based on the anti-inflammatory effect as described above, the composition of the present invention may be an anti-inflammatory pharmaceutical composition, an anti-inflammatory quasi-drug composition, an anti-inflammatory food composition, an anti-inflammatory food additive composition, an anti-inflammatory feed composition, an anti-inflammatory feed additive composition, or an anti-inflammatory cosmetic composition.

In addition, based on the anti-inflammatory effect as described above, the composition of the present invention may be a composition for preventing, ameliorating or treating inflammatory disease.

In this case, the inflammatory disease is not limited in the kind thereof, but may be selected from the group consisting of inflammatory lung disease, inflammatory liver disease, inflammatory bowel disease, autoinflammatory disease, inflammatory central nervous system disease, inflammatory skin disease, and allergic inflammatory disease. More specifically, the inflammatory disease may be selected from the group consisting of interstitial lung disease (ILD), non-alcoholic steatohepatitis (NASH), Crohn's disease, ulcerative colitis, rheumatoid arthritis, type 1 diabetes, lupus, multiple sclerosis, Parkinson's disease, scleroderma and psoriasis.

The composition of the present invention may be a composition containing the compound or salt thereof of the present invention, alone or in combination with a pharmaceutically acceptable carrier, a food-acceptable carrier, a feed-acceptable carrier or a cosmetically acceptable carrier.

The composition of the present invention may contain the compound or salt thereof of the present invention in an amount of 0.0001 to 100 wt % based on the total weight of the composition.

For clinical administration, the composition of the present invention may be administered orally or parenterally. For parenteral administration, the composition of the present invention may be administered by intraperitoneal injection, intrarectal injection, subcutaneous injection, intravenous injection, intramuscular injection, intrauterine dural injection, cerebrovascular injection or intrathoracic injection, and may be used as a general pharmaceutical formulation.

The composition of the present invention may be used alone or in combination with surgery, radiation therapy, hormone therapy, chemotherapy and a biological response modulator.

The daily dose of the compound or salt thereof contained in the composition of the present invention may be about 0.0001 to 100 mg/kg of body weight, or 0.001 to 10 mg/kg of body weight, and the composition of the present invention may be administered once or several times a day, and the dose thereof may vary depending on the subject's body weight, age, sex, health condition, diet, the period of administration, the mode of administration, excretion rate, and the severity of the disease.

For clinical administration, the composition of the present invention may be prepared as various oral or parenteral formulations by using diluents or excipients, such as fillers, extenders, binders, wetting agents, disintegrants, surfactants, etc., which are generally used.

In addition, the composition of the present invention may further contain, in addition to the composition or salt thereof of the present invention, one or more active ingredients exhibiting the same or similar function.

Hereinafter, the present invention will be described in more detail with reference to examples. However, these examples are only to illustrate the present invention in more detail and are not intended to limit the scope of the present invention.

EXAMPLES

1. Effect on Expression of NOX4 in Pulmonary Fibroblasts

Using diseased human lung fibroblasts (DHLFs) isolated from idiopathic pulmonary fibrosis patients, transcriptomes were analyzed comparatively between a group treated with TGF-β (10 ng/ml) and a group treated with TGF-β (10 ng/ml)+the compound (Formula 2) (50 μM) of the present invention.

More specifically, genes were selected whose expression was up-regulated at $p<0.005$ upon the treatment of the pulmonary fibroblasts with TGF-β and whose up-regulated expression was inhibited when the cells were treated with the compound of the present invention.

As a result, it was confirmed that the selected genes included NOX4.

NOX4 is a factor known to play an important role in inflammatory response by producing hydrogen peroxide (a major reactive oxygen species which is a secondary messenger of LPS signaling), and the above-described result implies that the compound of the present invention can alleviate inflammatory response occurring in the lungs.

In addition, based on the above result, it was determined that the compound of the present invention can be involved in major inflammatory responses other than that occurring in the lungs.

2. Effect on Expression of NOX4 in Hepatic Stellate Cells

Using the ONGHEPA1 cell line (KCTC13086BP) which is a mouse hepatic stellate cell line, the expression of NOX4 in a group treated with TGF-β (10 ng/ml) and a group treated with TGF-β (10 ng/ml)+the compound (Formula 2; 50 μM) of the present invention was compared by real-time PCR and immunocytochemistry (ICC).

Figure 2:
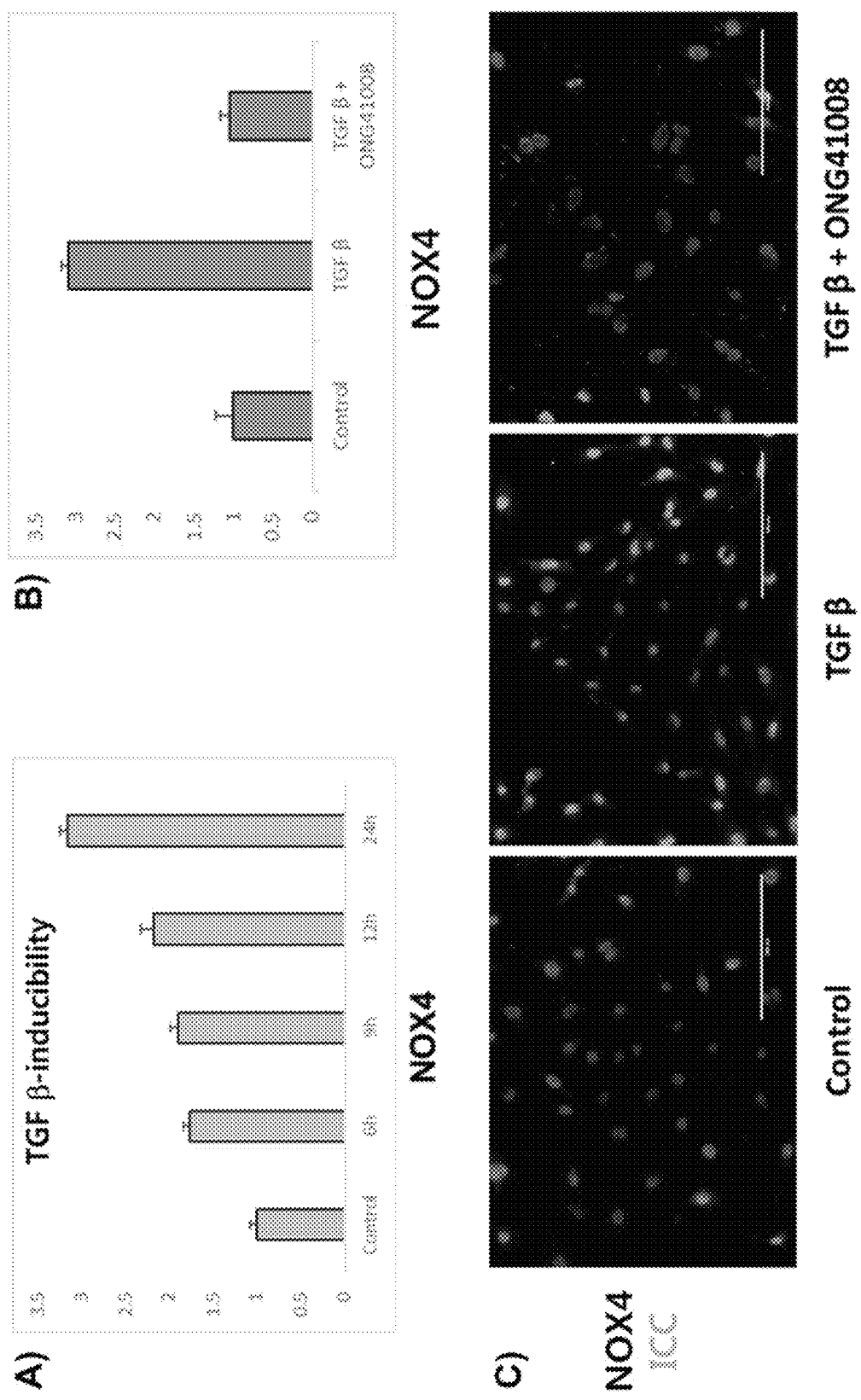
FIG. 2 shows the increase in expression of NOX4 in a mouse hepatic stellate cell line by TGF-β treatment and the inhibitory effect of the compound of the present invention on this increase. A): a graph showing the results of quantifying the time-dependent expression level of NOX4 by real-time PCR after treatment with TGF-β (10 ng/ml); B): a graph comparing the results of real-time PCR quantification of the expression level of NOX4 in a test group treated with TGF-β (10 ng/ml) alone and a test group treated with TGF-β (10 ng/ml)+the compound (Formula 2) (50 μM) of the present invention; C): images showing the results of immunocytochemistry (ICC) performed to analyze the expression level of NOX4 in a test group treated with TGF-β (10 ng/ml) alone and a test group treated with TGF-β (10 ng/ml)+the compound (Formula 2) (50 μM) of the present invention; Control: an untreated group; TGF β: a group treated with TGF-β (10 ng/ml); TGF β+ONG41108: a group treated with TGF-β (10 ng/ml) and the compound (Formula 2) (50 μM) of the present invention.

As a result, as shown in FIG. 2, it was confirmed that when the ONGHEPA1 cells were treated with TGF-β, the expression of NOX4 in the cells increased, and when the cells were treated with TGF-β+the compound of the present invention, this increase in the expression of NOX4 in the cells was inhibited.

Accordingly, it was confirmed that the compound of the present invention could alleviate inflammatory response occurring not only in the liver but also in the lungs, and thus it was determined that the compound of the present invention is highly likely to be involved in other major inflammatory responses.

3. Effect on Other Inflammation-Related Factors in Hepatic Stellate Cells

Using the ONGHEPA1 cell line, the production of reactive oxygen species (ROS) in a group treated with TGF-β (10 ng/ml) and a group treated with TGF-β (10 ng/ml)+the compound (Formula 2; 50 μM) of the present invention was compared by cell staining H2DCFDA (ThermoFischer, D399) which is a reactive oxygen species staining reagent, and the expression of CCL2 and CCL7 was compared by real-time PCR.

Reactive oxygen species are inflammation-inducing substances, and CCL2 and CCL7 are factors are involved in inflammatory response by recruitment of M1 type macrophages.

Figure 3:
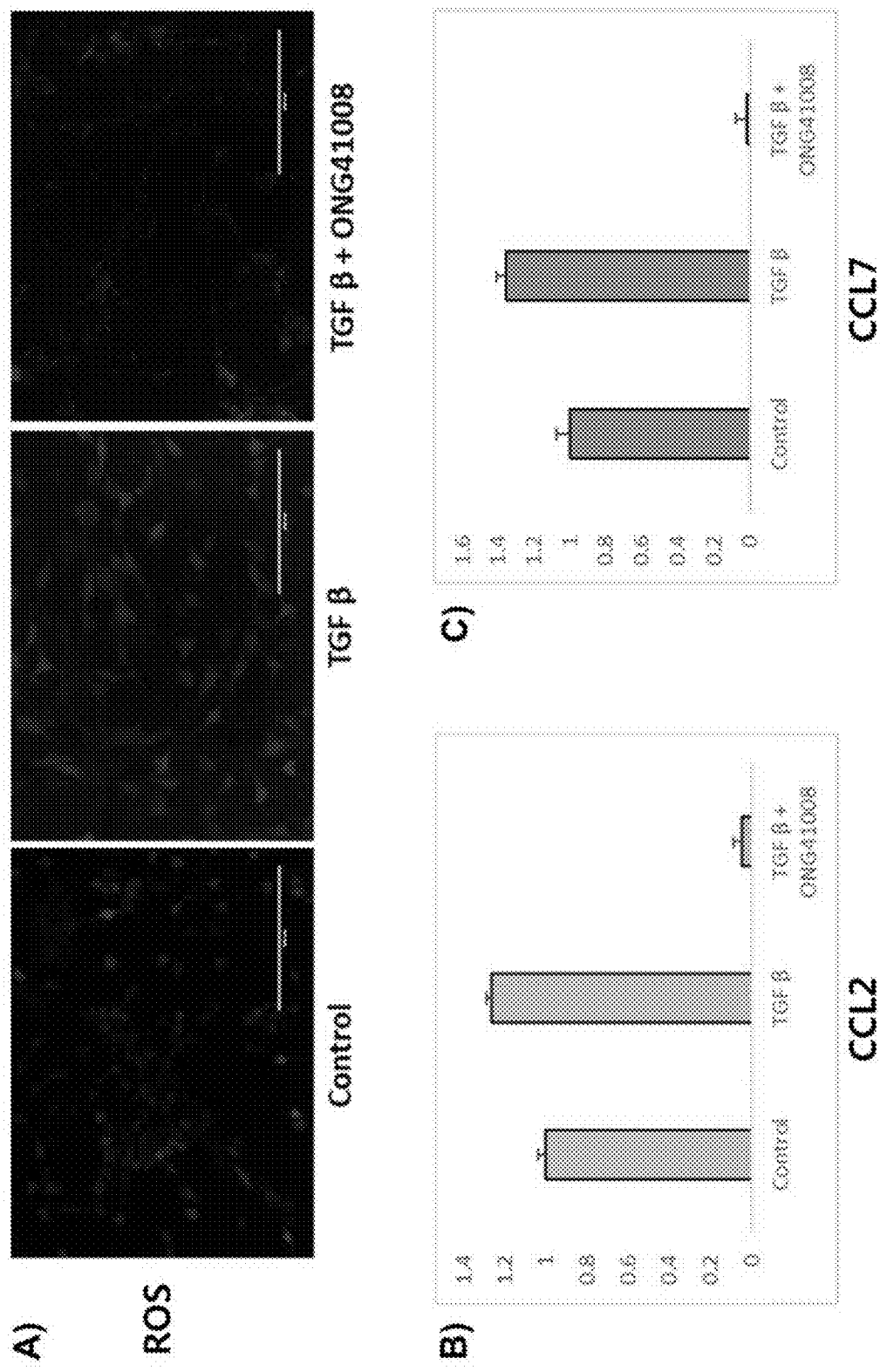
FIG. 3 shows the increases in ROS production, CCL2 expression and CCL7 expression in a mouse hepatic stellate cell line by TGF-β treatment, and the inhibitory effects of the compound of the present invention on these increases. A): images comparing the results of H2DCFDA staining performed to analyze ROS production in a test group treated with TGF-β (10 ng/ml) alone and a test group treated with TGF-β (10 ng/ml)+the compound (Formula 2) (50 μM) of the present invention; B): a graph comparing the results of real-time PCR quantification of the expression level of CCL2 in a test group treated with TGF-β (10 ng/ml) alone and a test group treated with TGF-β (10 ng/ml)+the compound (Formula 2) (50 μM) of the present invention; C): a graph comparing the results of real-time PCR quantification of the expression level of CCL7 in a test group treated with TGF-β (10 ng/ml) alone and a test group treated with TGF-β (10 ng/ml)+the compound (Formula 2) (50 μM) of the present invention; Control: an untreated group; TGF β: a group treated with TGF-β (10 ng/ml); TGF β+ONG41108: a group treated with TGF-β (10 ng/ml) and the compound (Formula 2) (50 μM) of the present invention.
Figure 4:
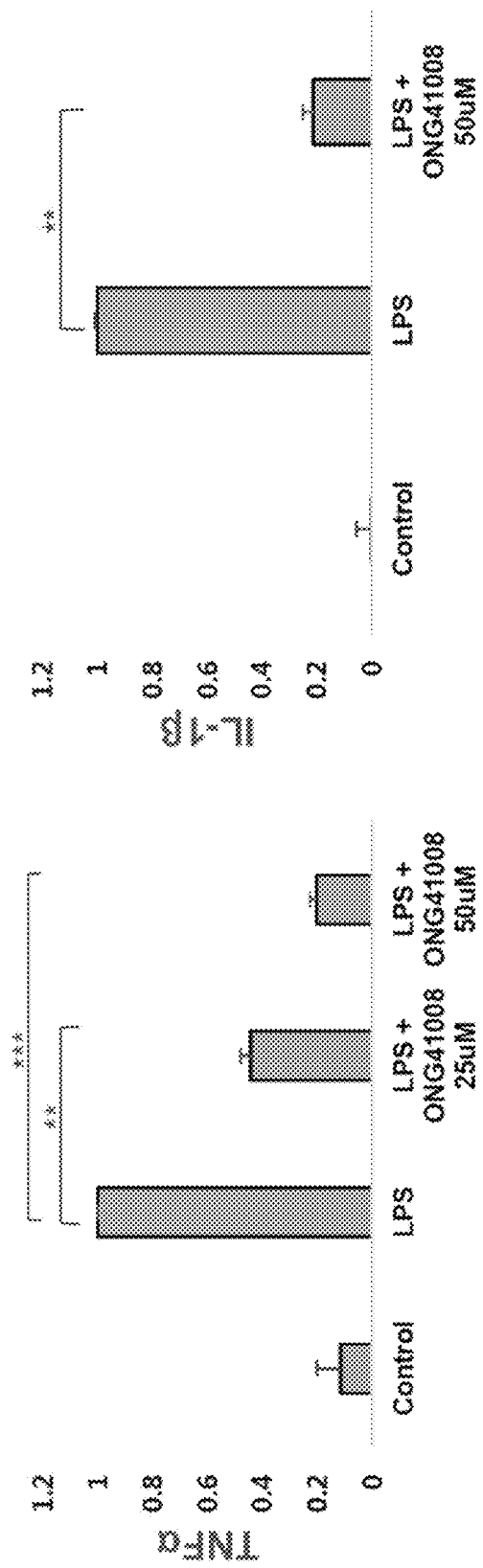
FIGS. 4 to 7 show the increases in expression of TNFα, IL-1β, CCL2 (MCP-1), CCL7 (MCP-3), CXCL2, CHOP and NOX1 in the RAW264.7 cell line by LPS treatment, and the inhibitory effects of the compound of the present invention on these increases. Control: an untreated group; LPS: a group treated with LPS (100 ng/ml); LPS+ONG41008: a group treated with LPS (100 ng/ml) and 25 μM or 50 μM of the compound (Formula 2) of the present invention. The graphs of FIGS. 4 to 6 and the left graph of FIG. 7 compare the results of real-time PCR quantification, and the right graph of FIG. 7 compares the results of ELISA (enzyme-linked immunosorbent assay) quantification.
Figure 5:
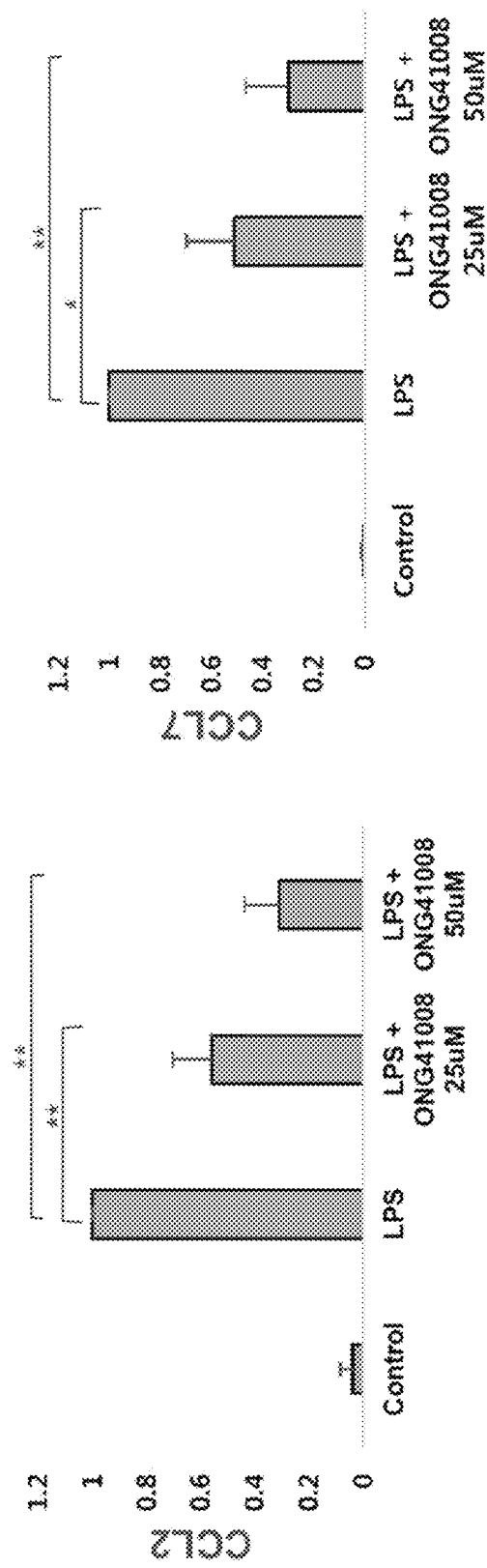
Figure 6:
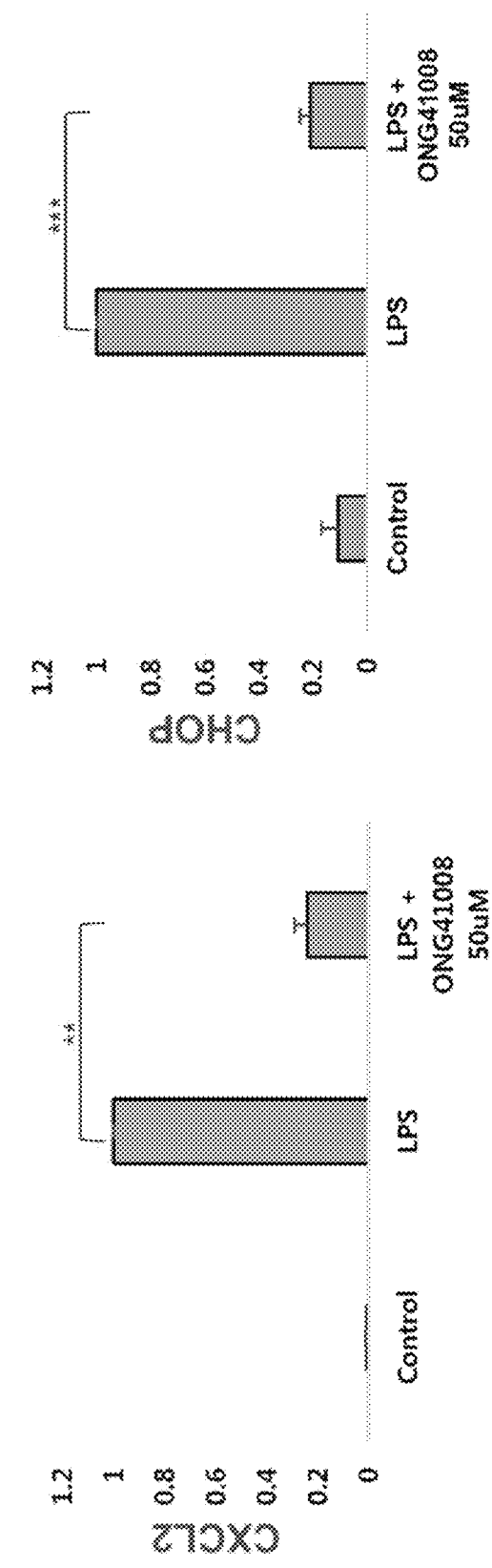
Figure 7:
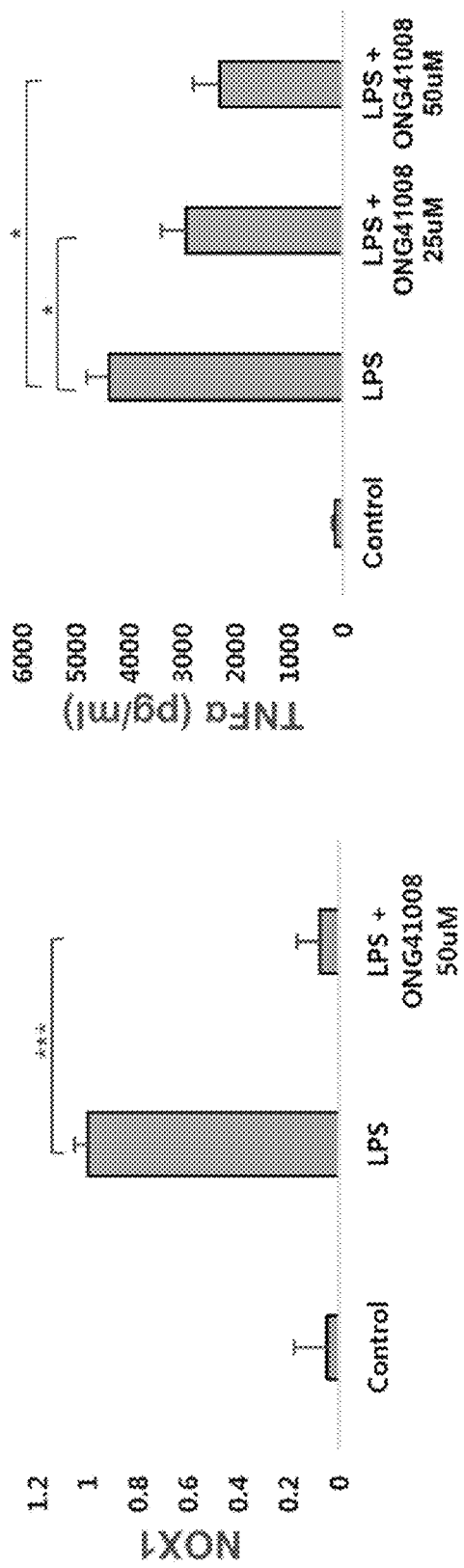

As a result, as shown in FIG. 3, it was confirmed that when the cells were treated with TGF-β, the production of reactive oxygen species and the expression of CCL2 and CCL7 increased, and when the cells treated with TGF-β+the compound of the present invention, these increases were inhibited.

Therefore, it was confirmed that the compound of the present invention controls not only NOX4 but also other inflammation-related factors.

4. Anti-Inflammatory Effect in Macrophages

In order to confirm the effect of the compound of the present invention in a special anti-inflammatory model, the anti-inflammatory effect of the compound of the present invention was examined using the RAW264.7 cell line (macrophage cell line).

Using the RAW264.7 cell line, the expression of inflammatory factors, INFα, IL-1β, CCL2 (MCP-1), CCL7 (MCP-3), CXCL2, CHOP and NOX1, in a group treated with LPS (lipopolysaccharide) and a group treated with LPS+the compound (Formula 2) of the present invention, was compared by real-time PCR or ELISA.

Specifically, the RAW264.7 cell line was cultured in RPMI liquid medium, and then divided into a normal control group (untreated), a group treated with LPS (100 ng/ml), and a group treated with the compound of the present invention (cells treated with 100 ng/ml of LPS and treated with 25 or 50 μM of the compound of the present invention). Each of the test groups treated was incubated for 24 hours, and then total RNA was extracted from the cell of each test group and synthesized into cDNA per 1 μg of total RNA, and real-time PCR for each inflammatory factor was performed. The real-time PCR was performed for 5 cycles, and then the obtained data were statistically processed using t-test.

As a result, as shown in FIGS. 4 to 7, it was confirmed that the expression of INFα, IL-1β, CCL2 (MCP-1), CCL7 (MCP-3), CXCL2, CHOP and NOX1 was increased by LPS treatment, and this expression was decreased by treatment with the compound of the present invention.

TNFα and IL-1β, which are pro-inflammatory cytokines produced in macrophages, are well known as very important factors in inflammatory response. CCL2 (MCP-1) and CCL7 (MCP-3), which are inflammatory cytokines, act to recruit M1 macrophages to the site of inflammation; CXCL2 is the most potent neutrophil-attractant chemokine; CHOP is an important transcription regulator in inflammasome production; and NOX1 (NADPH oxidase 1) is a factor that induces inflammation and cell destruction by producing reactive oxygen species (ROS) while existing in the plasma membrane, like NOX4. These factors are also known as very important factors in inflammatory response.

Thus, the above-described results show that the compound of the present invention can strongly inhibit inflammation by inhibiting the cause of inflammation and the mechanism of development of inflammation.

Figure 8:
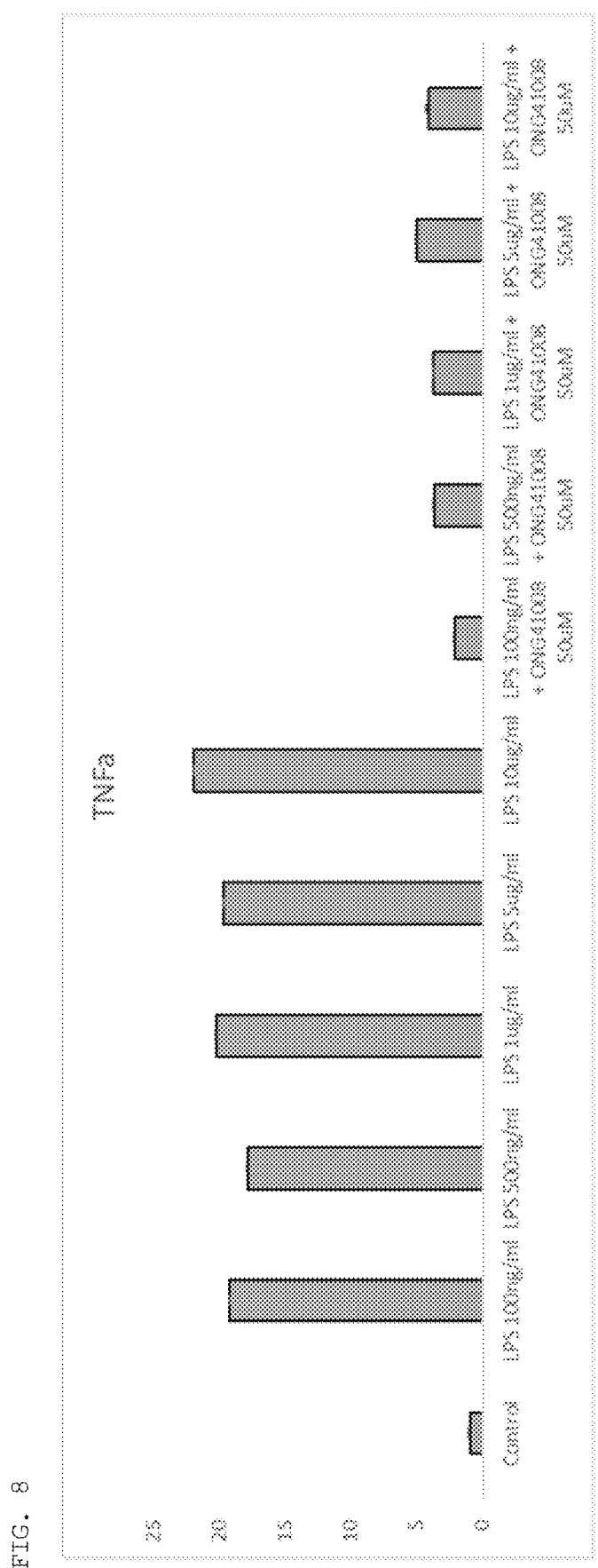
FIG. 8 is a graph showing the increase in TNFα expression in the RAW264.7 cells by treatment with various concentrations of LPS and comparing the results of quantifying the inhibitory effect of the compound of the present invention on this increase by real-time PCR. Control: an untreated group; LPS 100 ng/ml to LPS 10 μg/ml: groups treated with various concentrations of LPS; LPS 100 ng/ml+ ONG41008 50 μM to LPS 10 μg/ml+ONG41008 50 μM: groups treated with various concentrations of LPS and the compound (Formula 2) of the present invention.

In addition, according to the same method as described above, the RAW264.7 cell line was treated with various concentrations (100 ng/ml to 10 μg/ml) of LPS, and the effect of treatment with 50 μM of the compound (Formula 2) of the present invention was examined. As a result, as shown in FIG. 8, it was confirmed that the compound of the present invention blocked the expression of TNFα regardless of the concentration of LPS.

This result implies that the compound of the present invention can strongly inhibit inflammatory response regardless of the concentration of inflammation-causing substances.

Based on this result, it was determined that the compound of the present invention is likely to affect the cascade upstream of TNFα in inflammatory response. To verify this determination, the change in expression of an early inflammatory response stage factor (a factor involved in the early stage of LPS-induced inflammatory response) by treatment with the compound (Formula 2) of the present invention was examined by immunofluorescence staining using FITC.

As a result, as shown in FIGS. 9 to 12, it was confirmed that the compound of the present invention inhibited the activity of CD14 involved in the early stage of inflammatory response.

CD14 is known as a receptor of the inflammation inducer LPS together with LBP (LPS binding protein), TLR4, MD2 and the like. In addition, it is known that when the carboxyl terminus of CD14 binds to LPS-LBP, CD14 is dimerized rapidly and then separated from LBP, and CD14-LPS transfers LPS to MD2-TLR4, and then CD14-MD2-TLR4 undergoes endocytosis.

Figure 9:
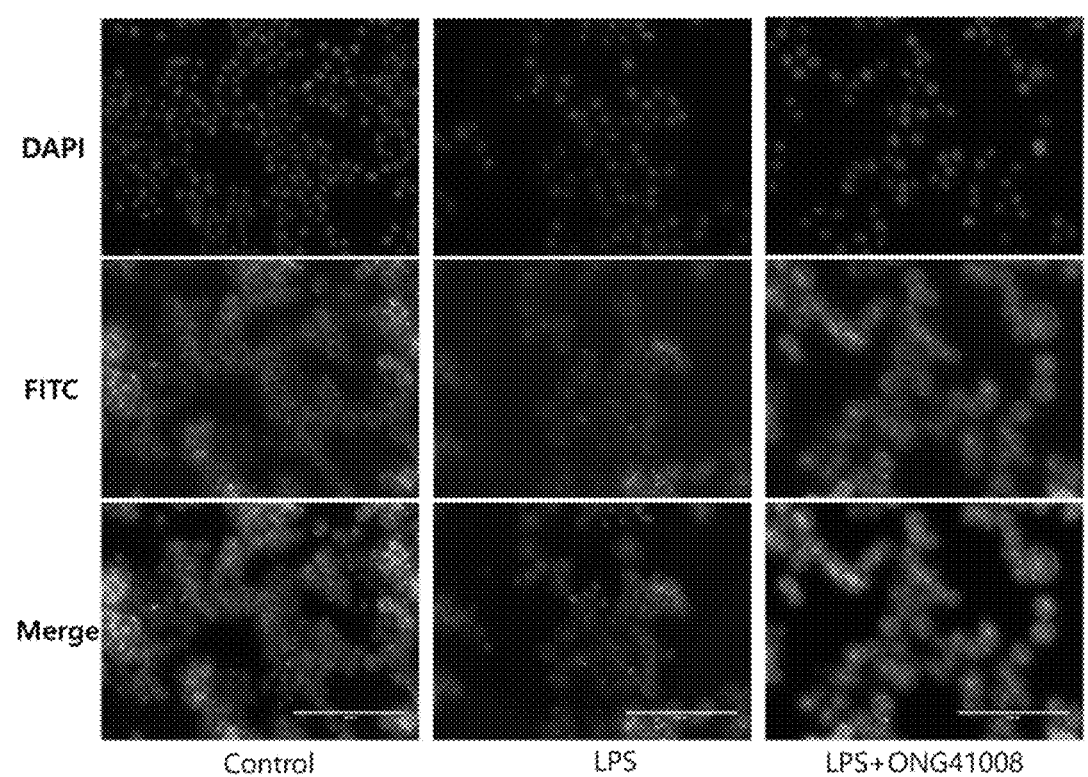
FIGS. 9 to 12 show the expression pattern of CD14 in the RAW264.7 cell line by LPS treatment, and show the results of FITC immunofluorescence staining and DAPI nuclear staining performed to the expression pattern of CD14 by treatment with LPS+the compound of the present invention. Control: an untreated group; LPS: a group treated with LPS (100 ng/ml); LPS+ONG41008: a group treated with LPS (100 ng/ml) and 50 μM of the compound (Formula 2) of the present invention; DAPI: the results of DAPI nuclear staining; FITC: the results of immunofluorescence staining; Merge: the results of merging the results of DAPI nuclear staining and the results of FITC immunofluorescence staining.
Figure 10:
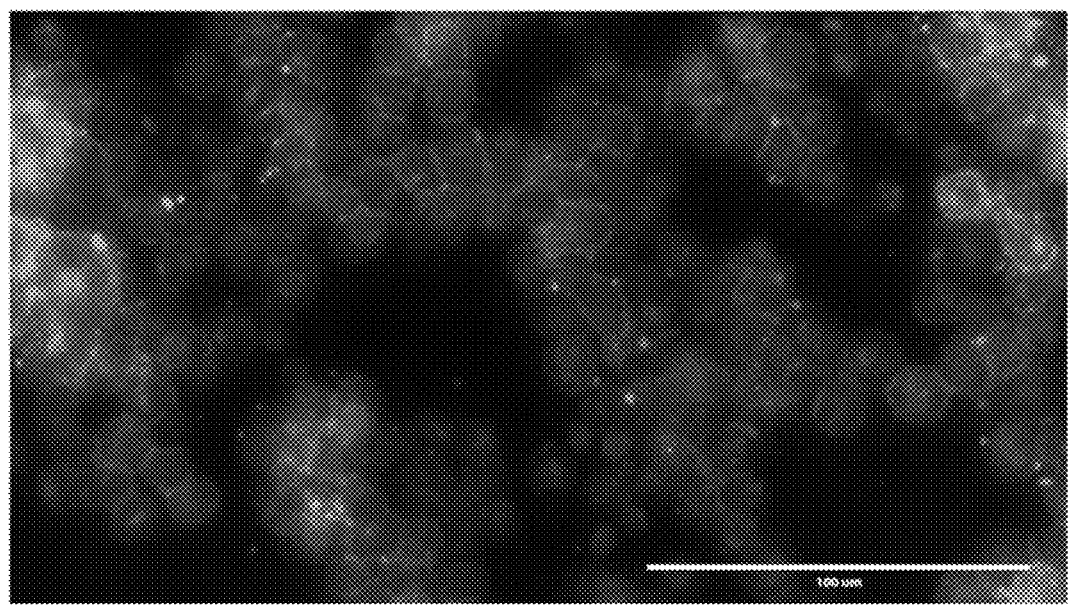
Figure 11:
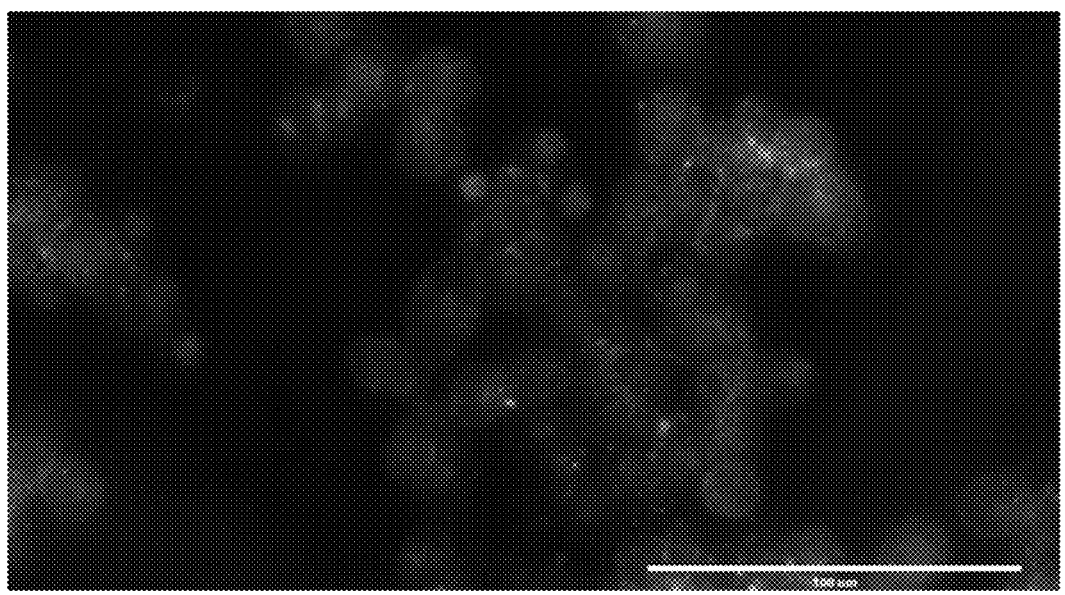
Figure 12:
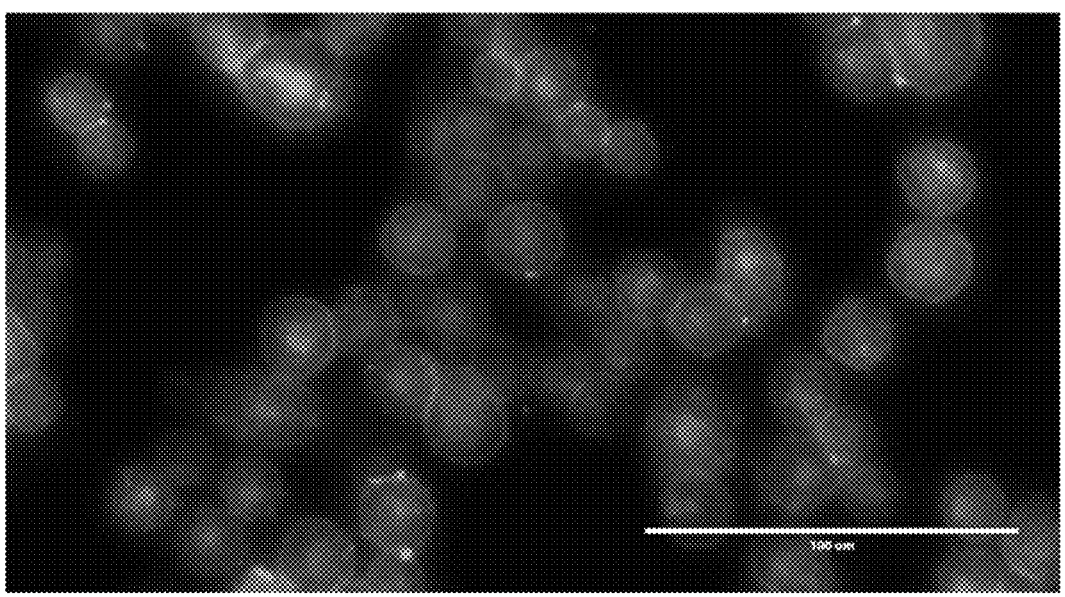

Looking at the control group in FIG. 9 (see FIG. 10 which is an enlarged view), it can be seen that FITC fluorescence is concentrated on the surface (membrane portion) of the cell. This indicates that CD14 is located on the surface of the cell under normal conditions. However, looking at the LPS-treated group (see FIG. 10 which is an enlarged view), it can be seen that the cell changes into a circular shape and FITC fluorescence is distributed throughout the cell without being concentrated on the surface of the cell. This means that when treated with LPS, CD14 did bind to LPS and endocytosis occurred. In the case of the group treated with the compound of the present invention (see FIG. 12 which is an enlarged view), the same pattern as that in the control group appeared despite LPS treatment. This indicates that endocytosis resulting from the interaction between CD14 and LPS did not occur, and thus the compound of the present invention blocked the interaction between CD14 and LPS.

Based on this result, it was determined that the compound of the present invention would be likely to bind to CD14 and block the interaction between CD14 and LPS. To verify this determination, a domain of CD14 to which the compound of the present invention can bind was analyzed, and whether or not the compound of the present invention is likely to structurally bind to the domain was analyzed.

Figure 13:
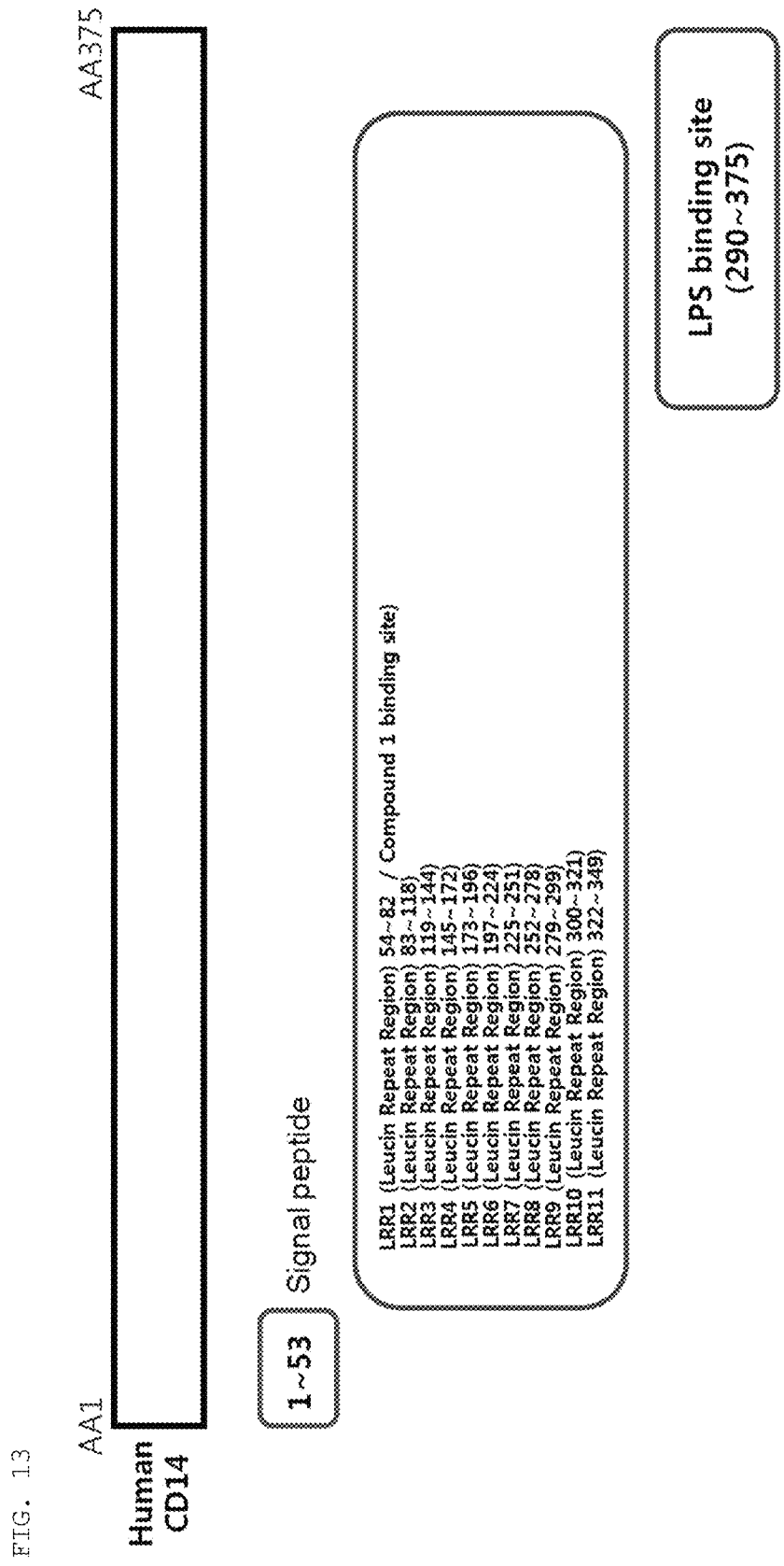
FIG. 13 shows the results of analyzing domains of human CD14.
Figure 14:
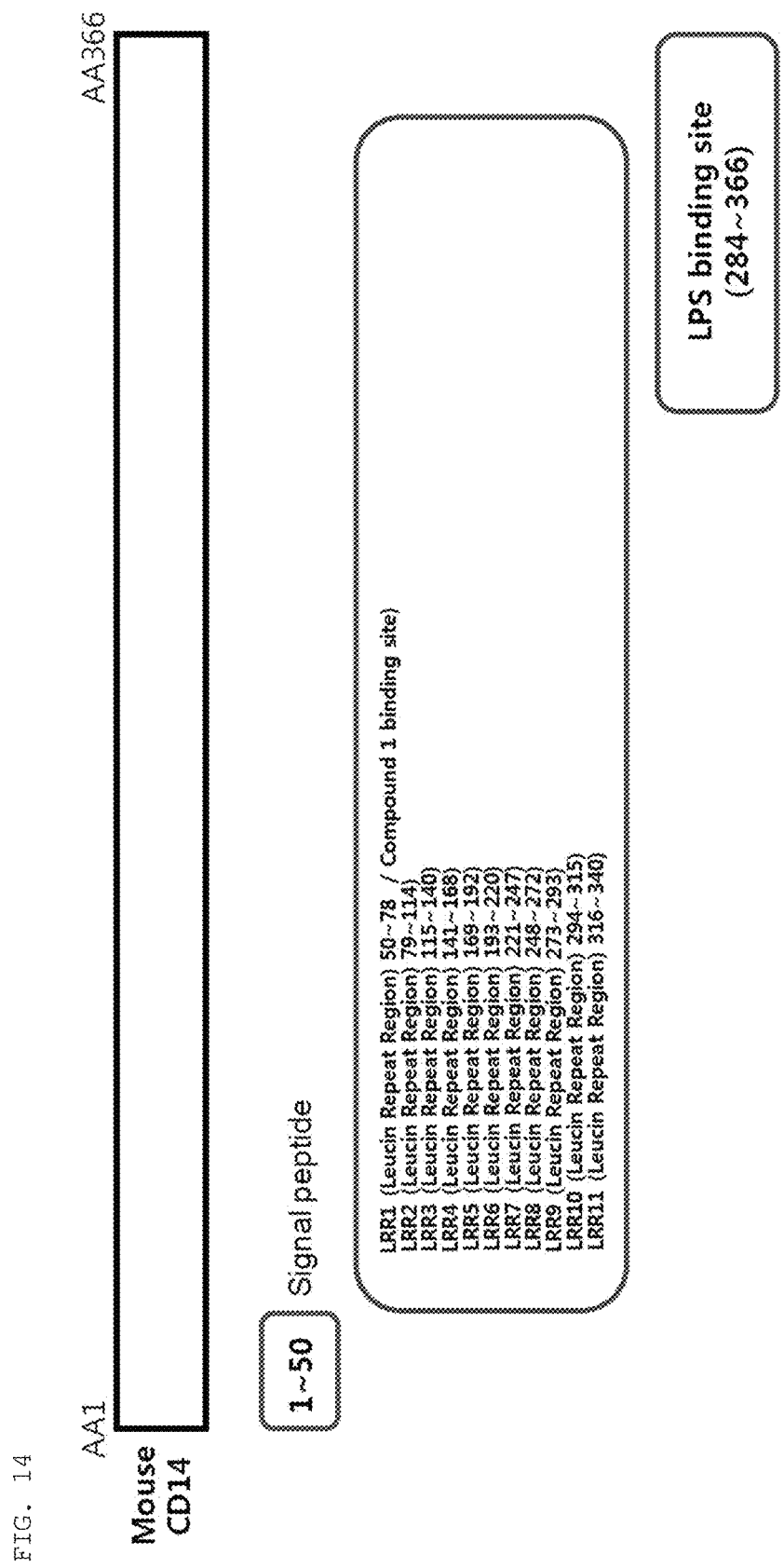
FIG. 14 shows the results of analyzing domains of mouse CD14.
Figure 15:
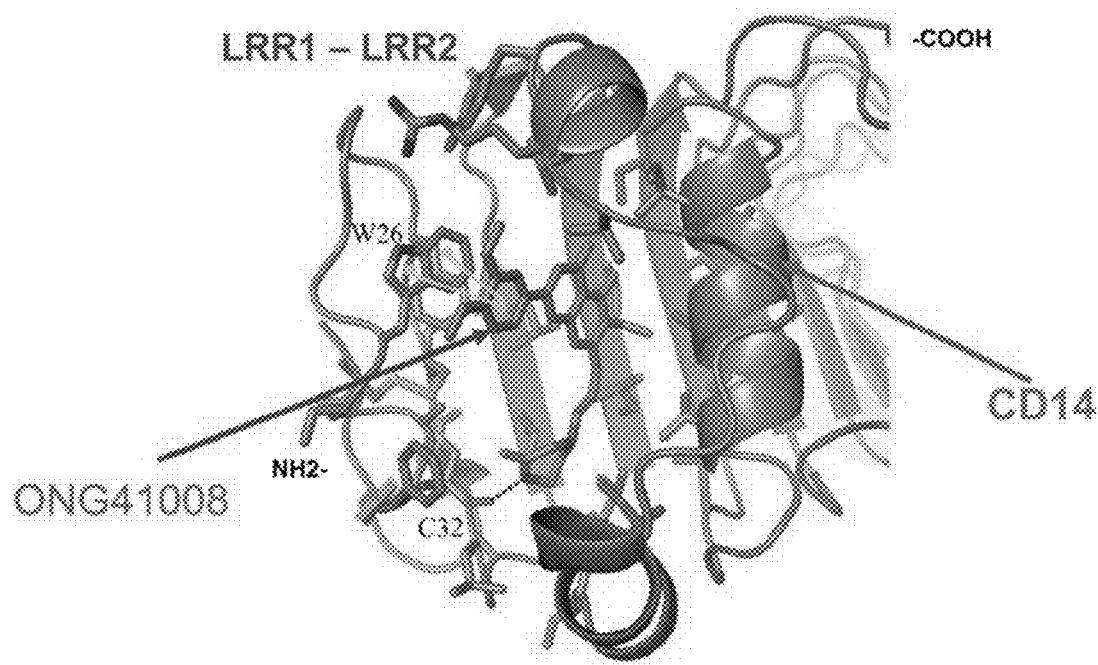
FIG. 15 shows a state in which the compound (Formula 2) (ONG41008) of the present invention binds to the LRR1-LRR2 domain of CD14.

As a result, as shown in FIGS. 13 to 15, it was confirmed that the piperazine structure of the compound of the present invention formed a hydrogen bond with the SH residue of the 32$^{nd}$ amino acid cysteine (C32) of CD14, and that the di-OMe-phenyl structure of the compound of the present invention formed an aromatic stacking interaction with the 26$^{th}$ amino acid tryptophan (W26) of CD14.

This supports that the compound of the present invention is highly likely to bind to CD14 and block the interaction between CD14 and LPS in inflammatory response.

Figure 16:
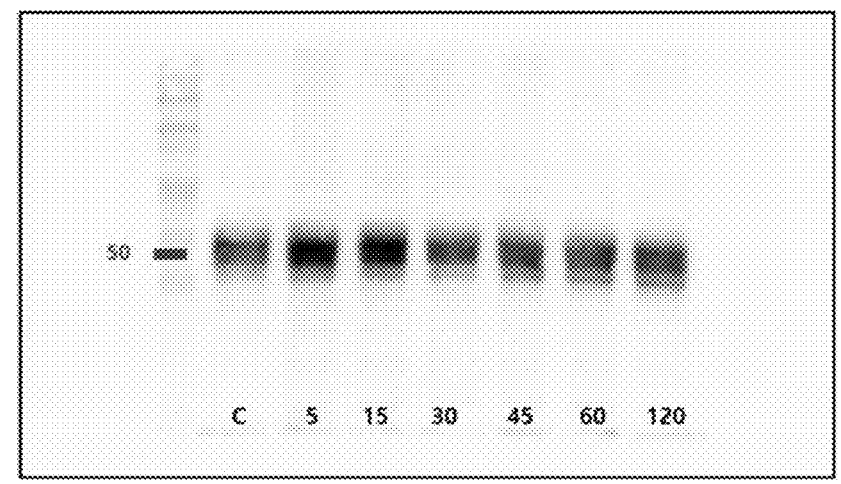
FIG. 16 shows the increase in CD14 expression in the RAW264.7 cell line by treatment with LPS (100 ng/ml), and the results of Western blot analysis performed to examine the inhibitory effect of the compound of the present invention on this increase. LPS (100 ng/ml): a group treated with LPS (100 ng/ml); LPS (100 ng/ml)+ONG41008 50 μM: a group treated with LPS (100 ng/ml) and 50 μM of the compound (Formula 2) of the present invention.
Figure 16:
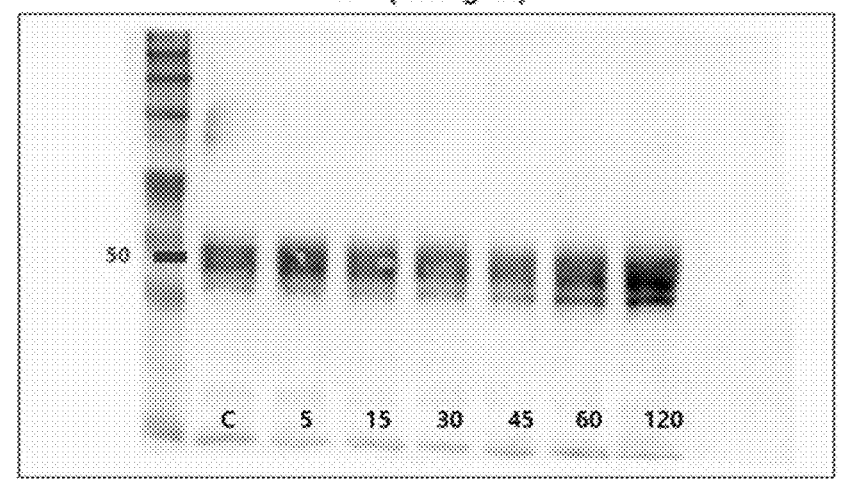
Figure 16:
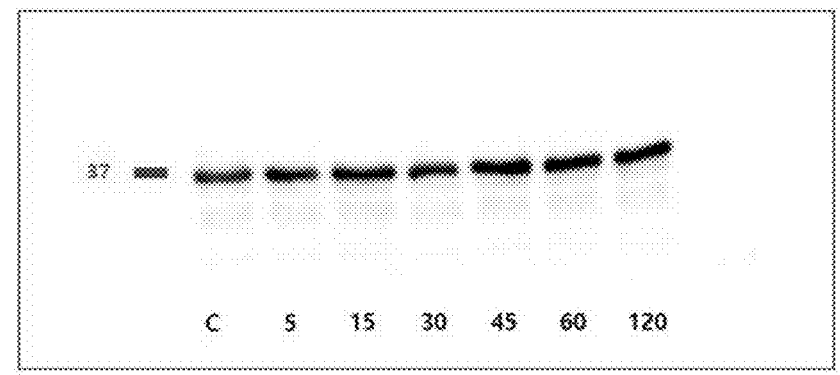

In addition, in order to examine the effect of the compound of the present invention on the expression of CD14, the expression of CD14 in a group treated with LPS (100 ng/ml) and a group treated with 50 μM of the compound (Formula 2) of the present invention was compared by Western blot analysis. As a result, as shown in FIG. 16, it was confirmed that LPS treatment increased the expression of CD14 after 5 to 15 minutes and that this increase in expression was decreased by treatment with the compound of the present invention.

This suggests that the compound of the present invention can exhibit a strong anti-inflammatory effect not only by inhibiting the activity of CD14 in inflammatory response, but also by inhibiting the expression of CD14 caused by inflammatory response.

As described above, the anti-inflammatory composition of the present invention can inhibit inflammatory response even at an early stage by inhibiting the interaction between CD14 and LPS and blocking the expression of CD14. In addition, the anti-inflammatory composition can inhibit the expression of TNFα and IL-1β, which are the key factors in inflammatory response, and can also regulate the expression of important factors, such as CCL2 (MCP-1), CCL7 (MCP-3), CXCL2, CHOP and NOX1, which are involved in inflammatory response. Thus, the anti-inflammatory composition of the present invention can exhibit a strong anti-inflammatory effect.

What is claimed is:

1. A method of treating an inflammatory disease in a subject in need thereof, comprising:
    administering to the subject in need there of a composition comprising, as an active ingredient, a compound represented by the Formula 1:

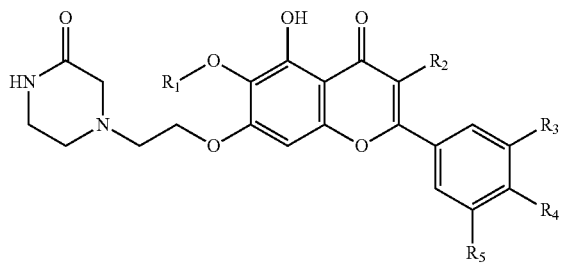

[Formula 1]

or a salt thereof,
    wherein $R_1$ is $C_{1-5}$ alkyl, $C_{5-6}$ cycloalkyl, $C_{5-6}$ heterocycloalkyl, $C_{6-12}$ aryl or $C_{5-6}$ heteroaryl, where the $C_{5-6}$ heterocycloalkyl or $C_{5-6}$ heteroaryl each independently contain at least one heteroatom selected from the group consisting of oxygen and nitrogen;
    $R_2$ is hydrogen, ethyl, acetyl, acetoxy, carboxy, benzoyloxy or 3,4,5-trihydroxybenzoyloxy;
    $R_3$ is hydrogen, hydroxy, methyl, methoxy, acetoxy, carboxy or benzoyloxy;
    $R_4$ is hydrogen, hydroxy, methyl, methoxy, acetoxy, carboxy or benzoyloxy; and
    $R_5$ is hydrogen, hydroxy, methyl, methoxy, acetoxy, carboxy or benzoyloxy,
    wherein the inflammatory disease is selected from the group consisting of Crohn's disease, ulcerative colitis, rheumatoid arthritis, lupus, multiple sclerosis and psoriasis.

2. The method of claim 1, wherein $R_1$ is methyl, ethyl, cyclopentyl, cyclohexyl or phenyl.

3. The method of claim 1, wherein
    $R_1$ is methyl;
    $R_2$ is hydrogen;
    $R_3$ is hydrogen, hydroxy or methoxy;
    $R_4$ is hydroxy or methoxy; and
    $R_5$ is hydrogen, hydroxy or methoxy.

4. The method of claim 1, wherein the compound is selected from the group consisting of Formula 2, Formula 3, Formula 4 and Formula 5:

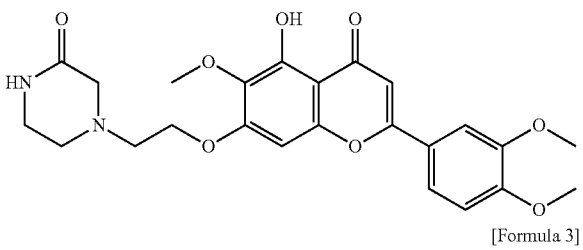

[Formula 2]

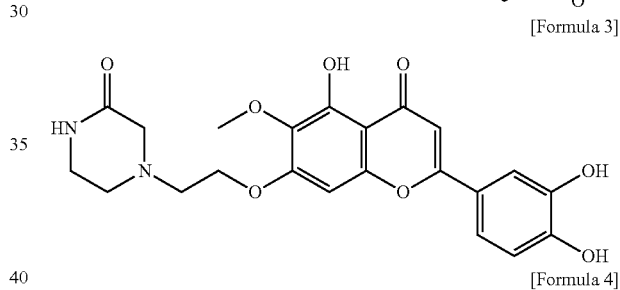

[Formula 3]

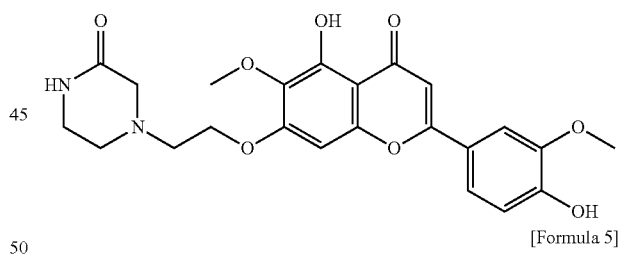

[Formula 4]

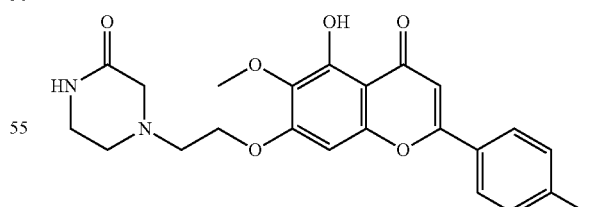

[Formula 5]

or a salt thereof.

5. The method of claim 1, wherein the composition is a pharmaceutical composition, a quasi-drug composition, a food composition, a food additive composition, a feed composition, a feed additive composition, or a cosmetic composition.

* * * * *